United States Patent
Schleipen et al.

(10) Patent No.: US 9,285,303 B2
(45) Date of Patent: Mar. 15, 2016

(54) OPTICAL BIOSENSOR WITH A PLURALITY OF SENSOR REGIONS AND A DETECTOR HAVING A DETECTOR PLANE WHEREIN AT LEAST ONE PRIMARY IMAGE IS MAPPED ONTO THE WHOLE DETECTOR PLANE

(75) Inventors: Johannes Joseph Hubertina Barbara Schleipen, Eindhoven (NL); Jacobus Hermanus Maria Neijzen, Heeze (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 91 days.

(21) Appl. No.: 14/342,058

(22) PCT Filed: Aug. 27, 2012

(86) PCT No.: PCT/IB2012/054380
§ 371 (c)(1),
(2), (4) Date: Feb. 28, 2014

(87) PCT Pub. No.: WO2013/035009
PCT Pub. Date: Mar. 14, 2013

(65) Prior Publication Data
US 2014/0217268 A1    Aug. 7, 2014

Related U.S. Application Data

(60) Provisional application No. 61/531,146, filed on Sep. 6, 2011.

(51) Int. Cl.
| | | |
|---|---|---|
| *G01N 21/01* | (2006.01) | |
| *G01N 21/25* | (2006.01) | |
| *G02B 21/02* | (2006.01) | |
| *G01N 21/552* | (2014.01) | |
| *G02B 3/00* | (2006.01) | |

(52) U.S. Cl.
CPC .............. *G01N 21/01* (2013.01); *G01N 21/253* (2013.01); *G02B 21/02* (2013.01); *G01N 21/552* (2013.01); *G02B 3/0056* (2013.01); *G02B 3/0062* (2013.01)

(58) Field of Classification Search
CPC ........... G01N 21/6452; G01N 33/0031; G02B 3/0062
USPC ........ 250/208.1, 216, 239, 221, 559.4, 458.1, 250/459.1; 356/317, 318; 435/287.1–287.4; 396/322, 323, 326, 331–333
See application file for complete search history.

(56) References Cited

U.S. PATENT DOCUMENTS

| | | | |
|---|---|---|---|
| 6,686,582 B1 | 2/2004 | Voelcker | |
| 7,560,270 B2 * | 7/2009 | Tanaami | 435/287.2 |
| 2010/0065726 A1 | 3/2010 | Zhong | |

FOREIGN PATENT DOCUMENTS

| | | |
|---|---|---|
| WO | 0101112 A1 | 1/2001 |
| WO | 0137012 A1 | 5/2001 |
| WO | 03098279 A2 | 11/2003 |
| WO | 2006079692 A1 | 8/2006 |
| WO | 2010150167 A1 | 12/2010 |

* cited by examiner

*Primary Examiner* — Que T Le

(57) ABSTRACT

The invention relates to an optical sensor device (100) that comprises a plurality of objectives (152) for generating primary images of corresponding sensor regions (111). The primary images are then mapped with intermediate optics (153) onto a detector plane (154), particularly onto the sensitive plane of an image sensor.

10 Claims, 3 Drawing Sheets

OPTICAL BIOSENSOR WITH A PLURALITY OF SENSOR REGIONS AND A DETECTOR HAVING A DETECTOR PLANE WHEREIN AT LEAST ONE PRIMARY IMAGE IS MAPPED ONTO THE WHOLE DETECTOR PLANE

CROSS-REFERENCE TO PRIOR APPLICATIONS

This application is the U.S. National Phase application under 35 U.S.C. §371 of International Application No. PCT/IB2012/054380, filed on Aug. 27, 2012, which claims the benefit of U.S. Provisional Patent Application No. 61/531,146, filed on Sep. 6, 2011. These applications are hereby incorporated by reference herein.

FIELD OF THE INVENTION

The invention relates to an optical sensor device, particularly a biosensor, comprising a plurality of sensor regions that shall be observed with a light detector.

BACKGROUND OF THE INVENTION

A biosensor of the aforementioned kind is known from the WO 2010/150167 A1. In the known biosensor, a plurality of lenslets are arranged in an array for focusing an incident parallel light beam that is generated by frustrated total internal reflection onto the sensor plane of an image sensor. Homogeneous images can be achieved this way that are not distorted by field curvature. However, detection NA is very low and the images obtained have a low resolution.

SUMMARY OF THE INVENTION

It is an object of the invention to provide an optical sensor device with an improved design, particularly a design that allows an observation of a plurality of sensor regions with high resolution. Most preferably, the optical properties should allow for the detection of single magnetic beads.

This object is achieved by an optical sensor device according to claim 1 and claim 2. Preferred embodiments are disclosed in the dependent claims.

An optical sensor device according to the invention may in general serve for any sensing purpose of interest. In particular, it may serve for the optical investigation of samples, for example for the detection of target components in a biological sample. The sensor device comprises the following components:

a) A plurality of N>1 sensor regions, i.e. regions that shall optically be observed or processed. Typically, the sensor regions may be cavities or chambers in which a sample can be provided. Moreover, these cavities or chambers are preferably accommodated in an exchangeable cartridge.

b) A plurality of N objectives that are arranged such that each objective generates an image of one of the aforementioned sensor regions. For purposes of reference, these different images will in the following be called "primary images". Henceforth the term "objective" shall generally denote an optical system that generates a real optical image of an object. Usually each objective will generate a primary image of one and only one sensing region, and each objective will image another sensor region than the other objectives.

c) A light detector with a light-sensitive detector plane onto which said primary images are mapped. The light detector may comprise any suitable sensor or plurality of sensors by which light of a given spectrum can be detected, for example photodiodes, photo resistors, photocells, a CCD/CMOS chip, or a photo multiplier tube.

According to a preferred embodiment of the invention, the optical sensor device may further comprise optics that map primary images generated by the objectives onto the detector plane. Because these optics is arranged in the light path between the detector plane and the objectives, it will in the following be called "intermediate optics". In this embodiment there is a division of tasks between the objectives and the intermediate optics which allows for miniaturizing the objectives such that they can be brought close to each other and can image individual small sensor regions.

The described optical sensor device has the advantage that it allows for the generation of high resolution images of the sensor regions even if they are very close to each other and extend over a wide field of view. This is achieved by using dedicated objectives for a primary imaging of the sensor regions and by projecting these primary images (optionally with intermediate optics) onto a common detector plane. It should be noted that the incident light of the objectives is not required to be parallel, i.e. the sensor regions can for example also be imaged in the case of a dark field illumination.

A high optical resolution of the objectives is achieved if at least one (preferably all) of the objectives has (have) a numerical aperture NA>0.1, preferably NA>0.25. With these NA values it is possible to resolve structures of about 1 μm (or, strictly speaking, of 0.6λ/NA), for example paramagnetic beads that label biological target components.

At least one primary image may be mapped such that it fills the whole detector plane. Thus the spatial resolution of the detector (e.g. given by the number of available pixels) can optimally be exploited. Preferably all primary images are mapped in this way onto the whole detector plane. In this embodiment some means will typically be required that allow for a distinction between the images (e.g. by color or by illumination multiplexing).

According to another embodiment, at least two primary images are mapped onto non-overlapping regions of the detector plane. Preferably all primary images are mapped onto mutually non-overlapping regions of the detector plane. Hence a simultaneous observation of the individual images can be achieved.

In the most simple case, an objective may consist of just one single (focusing) lens. Preferably, at least one of the objectives consists however of a plurality of lenses, particularly spherical and/or aspherical lenses. This allows the generation of higher quality images with higher numerical aperture.

According to another embodiment of the invention, at least two (preferably all) of the objectives comprise lenses that are formed with WaferOptics®. In this way it is possible to realize miniaturized objectives with high precision of their mutual arrangement. The intermediate optics may be adapted to map all N primary images simultaneously onto (distinct sub-areas of) the detector plane. In another embodiment, the intermediate optics comprises a multiplexing unit for selectively mapping different sets of n<N primary images onto the detector plane. As an extreme case, one single primary image after the other can be mapped onto the detector plane, preferably in such a way that it completely fills said plane. In this way the resolution of the detector plane can optimally be exploited. Distinguishing between the different sets of primary images can be obtained e.g. by time multiplexing and/or wavelength multiplexing of the illumination source.

The intermediate optics may comprise different optical elements to achieve its function. These elements may comprise reflecting elements, for example mirrors, refracting elements, for example wedge like structures or prisms, and/or diffracting elements like gratings. These optical elements may be arranged such that a set of 1≤n≤N primary images is appropriately mapped (e.g. in a non-overlapping manner) onto the detector plane.

The optical sensor device may further comprise a light source, for example a laser or a light emitting diode (LED), for generating an input light beam that is directed towards the sensor regions, where it is for example totally internally reflected and/or scattered.

The aforementioned light source may optionally be adapted to selectively illuminate separate sensor regions. It may for example comprise a plurality of individual lighting elements that can selectively switched on and off and that emit light to different sensor regions. Alternatively a multiplexing optics (e.g. a moving mirror) may be arranged between the (single) light source and the sensor regions. In this embodiment, the presently illuminated sensor region(s) may be mapped onto the whole detector plane without being disturbed by images of the non-illuminated sensor regions.

The light detector preferably comprises a plurality of individual detector units, which will as usually be called "pixels" in the following. Such a pixelated light detector may particularly be realized by an image sensor, for example a CCD or CMOS device as it is known from digital cameras. A plurality of detector pixels allows to evaluate the information comprised by the output light beam in a spatially resolved way with respect to the investigation region.

According to another embodiment, the optical sensor device comprises an image processing unit, for example a microprocessor with associated software for digital image processing, said image processing unit being able to process images generated on the detector plane by the objectives and the intermediate optics.

The invention further relates to the use of the optical sensor device described above for molecular diagnostics, biological sample analysis, or chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiments described hereinafter.

In the drawings.

Like reference numbers refer in the Figures to identical or similar components.

DETAILED DESCRIPTION OF EMBODIMENTS

Figure 1:
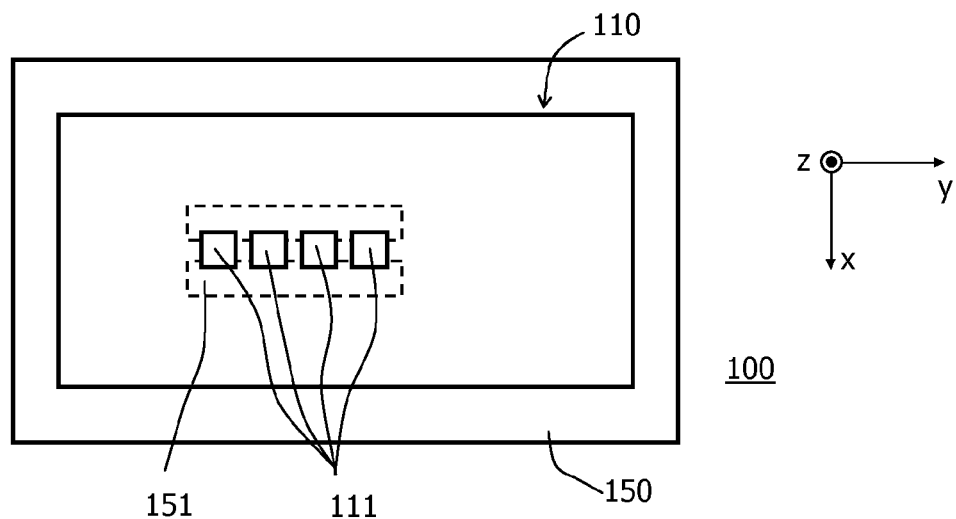
FIG. 1 schematically shows a top view of a sensor device according to the present invention.

The WO 2010/150167 A1 (which is incorporated into the present application by reference) describes an immuno-assay biosensing technology based on optical detection of superparamagnetic nanoparticles, henceforth called beads. Here, the magnetic properties of the nanoparticles are being used for (i) speeding up the diffusion process of analytes towards the detection surface and (ii) enabling a magnetic washing step where unbound nanoparticles are extracted from the detection zone prior to the optical detection. For detection frustrated total internal reflection may be used. Moreover, dark field detection of scattered light from substrate bound nanoparticles, also called single bead detection, may be used.

In the mentioned technologies a disposable plastic injection molded cartridge is used, comprising e.g. a blood filter, microfluidics for transportation of blood plasma towards a detection chamber, said detection chamber containing buffer constituents and nanoparticles, and optical windows for coupling in the excitation light needed for total internal reflection, and coupling out the frustrated total internal reflected (FTIR) beam for FTIR detection or the scattered light of bound nanoparticles for dark field detection.

For a single bead detection platform, simultaneous readout of multiple immunoassay reaction chambers is a key requirement. However, single bead imaging requires a moderate (>0.25) to high (>0.5) numerical aperture objective lens in order to resolve individual single beads (typical bead diameter used in a biosensor is about 500 nm). The problem when imaging with a high NA is that the available object field is limited. E.g. for a standard NA=0.25, M=10× microscope objective, the available field diameter is typically 2 mm. Since the detection of multiple reaction chambers requires an object field in the order of typically 5 mm or larger, standard objective lenses cannot be used. To be able to image large field areas one can basically do two things:

1. Enlarge the object field of the microscope objective by adding more lens elements and/or aspherical lens surfaces. Drawback of this method is a rather bulky and expensive objective lens, which is not the preferred solution for implementing in a hand-held, low-cost product.

2. Mechanically scanning the object underneath the microscope objective field. A general disadvantage of this method is the additional need for actuation mechanics and active focusing control. The different reaction chambers are then being readout in a time-multiplexed manner, one after the other. However, all chambers should preferably be readout continuously during the whole assay time, which means that the cartridge needs to be scanned back and forth constantly, having a negative effect on power consumption and system stability.

The alternative approach proposed here works (best) with a discrete set of sensor regions or chambers. According to this approach, this set of sensor regions or chambers is imaged individually, each with its own corresponding miniature objective. Since the area to be imaged by each objective is limited in this case to the size of a single sensor region (reaction chamber), which is typically 500 to 1000 μm, the required object field is also limited to this value.

FIGS. 1 to 4 schematically show an optical biosensor device 100 according to the present invention. The biosensor 100 comprises two main components, namely a removable and disposable cartridge 110 and an analyzer or reader 150. The cartridge 110 is typically made from glass or plastics by injection molding and comprises a microfluidic system that can be filled with a sample fluid like blood or saliva. In the Figures only four sensor regions or reaction chambers 111 of this microfluidic system are exemplarily shown. Additional channels for the transfer of sample, for venting and the like are not shown in detail.

The reader 150 comprises a plurality of objectives 152 that are disposed next to each other (in a plane traverse to their optical axes) in an arrangement corresponding to the arrangement of the sensor regions 111. Hence each objective 152 can generate a "primary image" of an associated sensor region 111. These primary images are then mapped or projected with a common intermediate optics 153 onto a detector plane 154. This may particularly be the plane of pixels of an image sensor, e.g. a CMOS or CCD device. The image generated in this detector plane 154 is transferred to an evaluation unit 155 for further processing and evaluation. The evaluation unit 155 may for instance be realized by a microprocessor with associated software.

Figure 3:
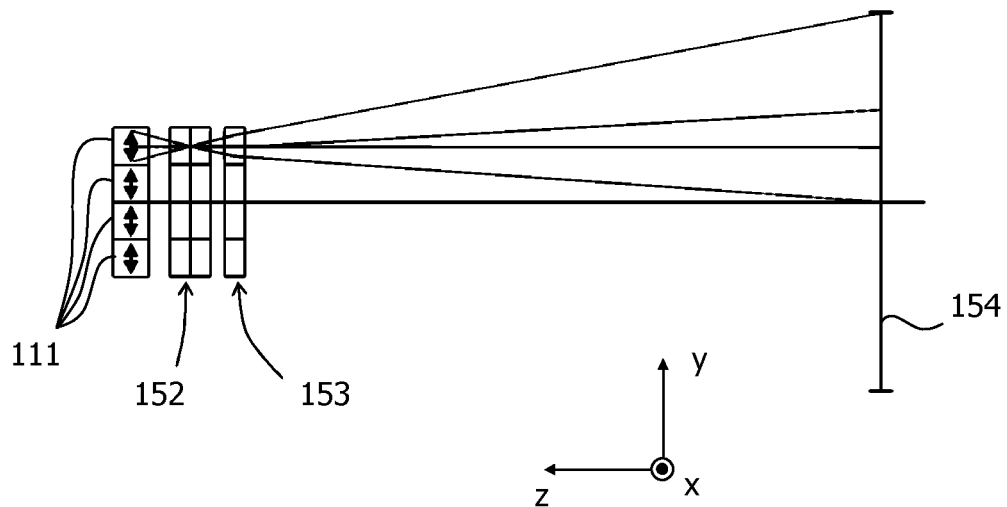
FIG. 3 is a simplified sketch of the optical paths of FIG. 2 showing that the primary images are mapped onto non-overlapping regions of the detector plane.
Figure 4:
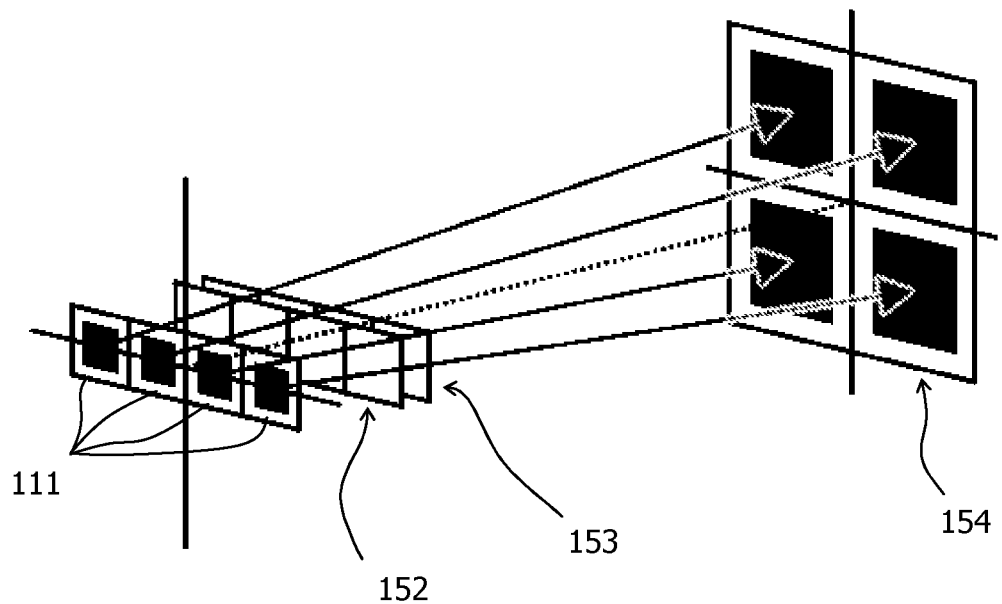
FIG. 4 is a perspective view corresponding to FIG. 3.

As can be clearly seen from the schematic drawings of the light paths in FIGS. 3 and 4, the primary images of the individual sensor regions 111 are mapped onto non-overlapping regions of the detector plane 154. Hence they can be recorded and evaluated simultaneously.

The reader 150 may further comprise a light source 156 for illuminating the sensor regions 111 with a light beam L. Light that is scattered by target components in the sensor regions may then be collected by the objectives 152. Moreover, the readout device 150 may comprise magnet yokes 151 disposed below the cartridge 110 such that a magnetic field can be generated in the sensor regions 111.

The spacing between individual sensor regions or reaction chambers 111 is preferably kept small due to the limited size of the sweet spot for homogeneous magnetic actuation. To be able to image the discrete set of closely spaced reaction chambers 111 without being obstructed by the imaging optics, the diameter of each objective 152 should be smaller than the reaction chamber spacing. This requires miniature lenses. The high to moderate NAs requires the objectives to have more than one lens element. An elegant solution which is very cost effective for mass manufacturing is offered by the WaferOptics® technology of Anteryon (Eindhoven, NL). This wafer scale manufacturing process enables the production of a large volume of optical elements on a single glass wafer. These micro optical elements can be refractive such as (a)spherical, (a)cylindrical or free-form lenses or diffractive optical elements.

Using these miniature scale optical components has two additional advantages:

Optical aberrations in general become smaller with decreasing aperture size. Using small aperture wafer optics enables the realization of a NA=0.25 objective lens with only two, possibly three lens elements (i.e. two or three wafers stacked on top of each other). Furthermore Anteryon's technology (using glass-polymer photo-replication) allows the application of aspherical surfaces, correcting for spherical aberration and coma at these high NAs.

Figure 2:
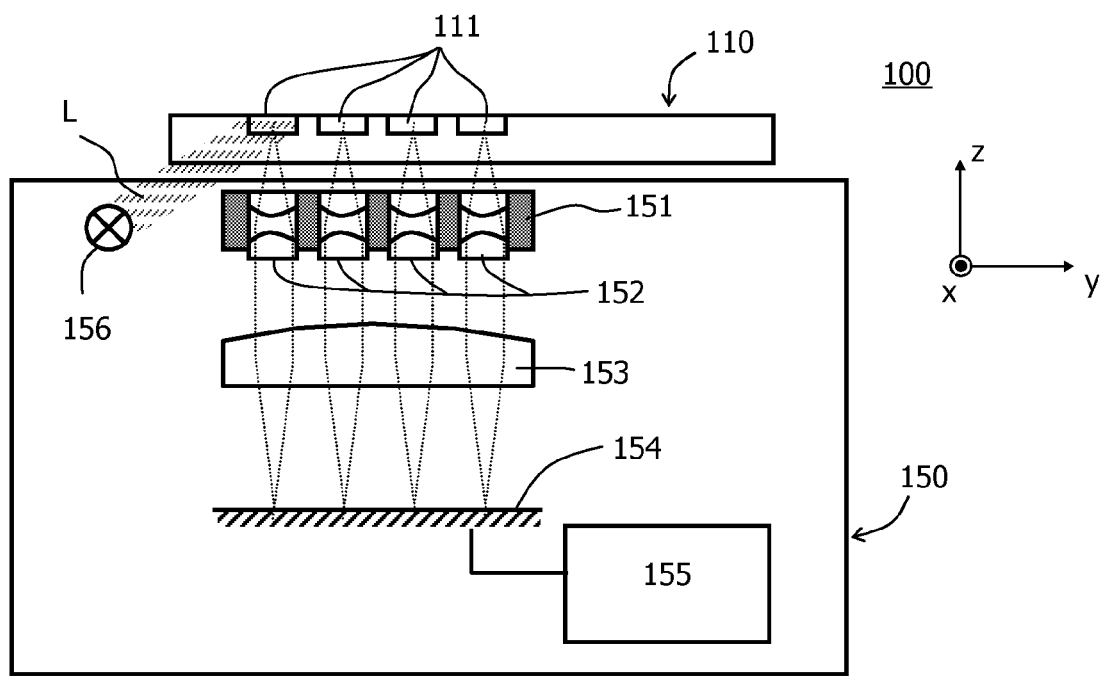
FIG. 2 shows a schematic side view of the sensor device of FIG. 1.

Since the diameter of the individual objective lenses can be kept low, they can easily be mounted just underneath a horse shoe magnet of the single bead biosensor setup, or even in between the two pole tips of the horseshoe magnet (as shown in FIGS. 1 and 2).

In summary, the invention proposes a division of the several millimeters large object space into subspaces, as indicated in FIGS. 2 to 4. Each subspace covers a single immunoassay reaction chamber 111 and is being imaged by a corresponding miniature objective 152. Feasibility of making a NA=0.25 objective lens using miniature optics could be shown with a stack of two wafers, having four refracting surfaces, out of which three or four surfaces have been equipped with an aspherical layer. The object field that needs to be imaged has a diameter of e.g. 0.5 mm. The maximum field coordinate is 0.25 mm and the object is preferably imaged at infinity.

Figure 5:
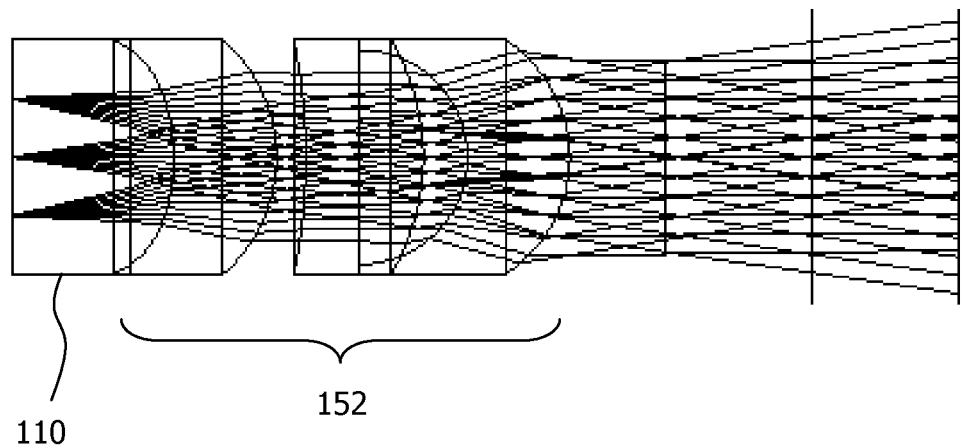
FIG. 5 shows exemplary paths of light rays in an objective according to the invention.

FIG. 5 shows an exemplary 3-element miniature objective lens design with an object field of 0.8 mm (full field of view; infinite conjugate; NA=0.25). The required clear aperture for this design is 1.8 mm, thereby fitting in a 2×2 mm square optical component.

When imaging a set of objects using a discrete set of objective lenses, a discrete set of subimages will be formed. These subimages preferably need to be imaged onto a single detector. For this some dedicated detector imaging optics ("intermediate optics") is required. The exact optical functionality of this optics depends on:

(i) Whether the individual subimages ("primary images") need to be imaged onto the detector at the same time, or each subimage is imaged onto the full sensor area using some multiplexing scheme, e.g. time multiplexing where each detection chamber is illuminated and the corresponding image is readout sequentially.

(ii) The layout of the reaction chambers inside the cartridge, e.g. whether the chambers are positioned along a line (full object field typically 8×1 mm), or in a square (full field typically 3×3 mm). When a horseshoe magnet with a rather elongated and narrow air gap is used, the arrangement of the reaction chambers will preferably be along a line.

(iii) The actual design of the miniature objective lenses, and the corresponding location of the subimage being formed by each miniature objective lens. In the case of an infinite conjugate objective lens design all (e.g. four) subimages will be positioned at infinity and the final images made by a single detector lens 153 ("intermediate optics") will be overlapping at the detector plane.

Figure 6:
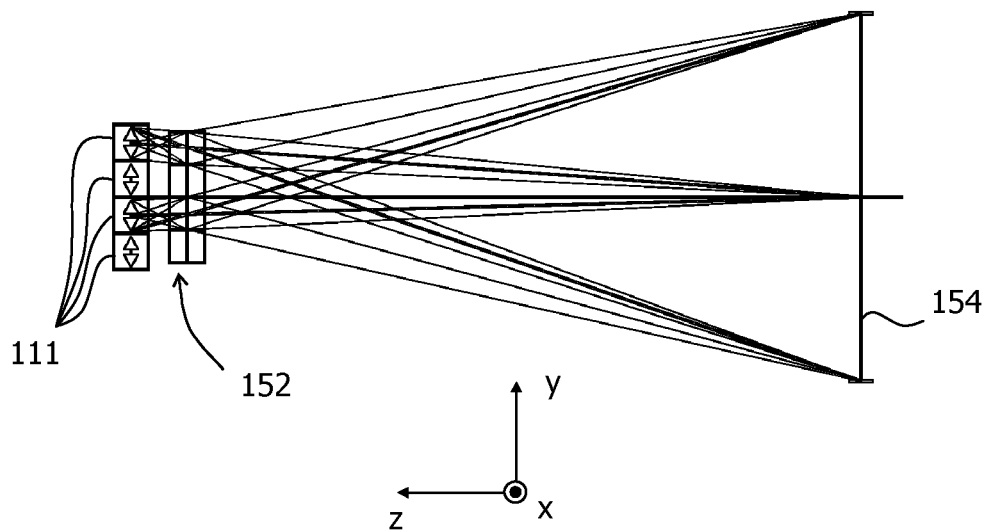
FIG. 6 is a simplified sketch of the optical paths of a sensor device in which the primary images are mapped onto the whole detector plane.

In the case of e.g. time multiplexing a single detector lens 153 may be used to image the subimages onto the detector one after another. FIG. 6 shows an alternative embodiment of this approach in which no intermediate optics is used. The primary images generated by an objective lens array 152 are directly mapped onto the detector plane 154, wherein each primary images fills the whole plane. In order to distinguish between the individual images, illumination multiplexing can for example be used.

When all subimages need to be imaged onto the detector at the same time, some additional optics needs to be incorporated in the intermediate optics between objective lenses 152 and detector plane 154, redirecting (i.e. tilting) and magnifying each subimage to its appropriate location on the detector plane. For the tilting/redirecting part reflective (mirrors) as well as refractive (wedge-like structures) or diffractive (e.g. gratings) optics may be used. In the latter two cases, these wedge-like structures or gratings may be incorporated in the detector lens 153. If more subimages are imaged onto the detector at the same time, the ultimate resolution will go down accordingly for a constant size detector, unless the number of pixels is increased as well.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An optical sensor device, comprising:
   a) a plurality of sensor regions;
   b) a plurality of objectives that are arranged such that each objective generates a primary image of one of the sensor regions,
   wherein at least one of the objectives has a numerical aperture larger than 0.1 and comprises several lenses;
   c) a light detector with an array of detector pixels;
   d) intermediate optics that maps primary images of the objectives onto the detector plane, wherein at least one primary image is mapped onto the whole detector plane; and
   e) a light source for generating an input light beam (L) that is directed towards the sensor regions.

2. An optical sensor device, comprising:
   a) a plurality of sensor regions;
   b) a plurality of objectives that are arranged such that each objective generates a primary image of one of the sensor regions; and
   c) a light detector with an array of detector pixels as detector plane onto which said primary images are mapped, wherein at least one primary image is mapped onto the whole detector plane.

3. The optical sensor device according to claim 1, wherein at least one of the objectives has a numerical aperture larger than 0.1, preferably larger than 0.25.

4. The optical sensor device according to claim 1, wherein at least one of the objectives comprises several lenses.

5. The optical sensor device according to claim 1, wherein the intermediate optics comprises a multiplexing unit for selectively mapping different sets of primary images onto the detector plane.

6. The optical sensor device according to claim 1, wherein the intermediate optics comprises reflecting, refracting, and/or diffracting elements.

7. The optical sensor device according to claim 1, wherein the light source configured to generate the input light beam (L) that is totally internally reflected and/or scattered at the sensor regions.

8. The optical sensor device according to claim 7, wherein the light source is adapted to selectively illuminate separate sensor regions.

9. The optical sensor device according to claim 1, wherein the detector plane comprises an array of detector pixels.

10. The optical sensor device according to claim 1, further comprising an image processing unit configured to process images generated on the detector plane.

* * * * *